United States Patent [19]

Li et al.

[11] Patent Number: 5,395,624
[45] Date of Patent: Mar. 7, 1995

[54] DEPIGMENTING COSMETIC AND/OR DERMATOLOGICAL COMPOSITION CONTAINING A DI- OR TRI-CAFFEOYLQUINIC ACID, OR A MIXTURE THEREOF

[75] Inventors: Ming Li, Gif sur Yvette; Thierry Sevenet, Paris; Hubert Schaller, Selestat; Hamid Abdul Hadi, Gif sur Yvette; Daniel Guenard, Montrouge; Pierre Potier; Eric Pilleux, both of Paris, all of France

[73] Assignee: L'Oreal, Paris, France

[21] Appl. No.: 83,376

[22] Filed: Jun. 29, 1993

[30] Foreign Application Priority Data

Jul. 1, 1992 [FR] France ................ 92 08091

[51] Int. Cl.$^6$ .................. A61K 9/127; A61K 7/00
[52] U.S. Cl. .................. 424/450; 424/401; 424/62; 514/568; 514/569; 514/944
[58] Field of Search ............ 514/568, 569, 944; 424/450, 62, 401

[56] References Cited

U.S. PATENT DOCUMENTS 4,865,847 9/1989 Gosswein .................. 424/439

FOREIGN PATENT DOCUMENTS 4169526 6/1992 Japan.
9105543 5/1991 WIPO.

OTHER PUBLICATIONS

Shiseido Chem. Abstrs. 117, 1992 (184886g).

Salo et al., Chemical Abstracts, vol. 79, No. 27209, 1973.
Revesti Chemical Abstracts, vol. 67, No. 57236, 1969.

Primary Examiner—Gollamudi S. Kishore
Attorney, Agent, or Firm—Oliff & Berridge

[57] ABSTRACT

A depigmenting cosmetic or dermatological composition containing, as active ingredient, at least one di- or tri-caffeoylquinic acid corresponding to general formula (I):

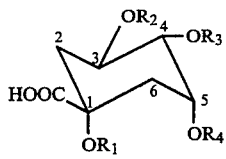

in which:
$R_1$, $R_2$, $R_3$, and $R_4$ represent a hydrogen atom or the CAF radical corresponding to the formula:

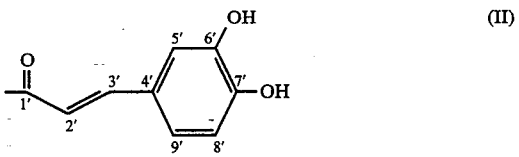

provided that at least two, and at most three, of the $R_1$, $R_2$, $R_3$, and $R_4$ radicals represent the CAF radical, but excluding $R_1$ and $R_4$ as representing the CAF radical and $R_2$ and $R_3$ as representing a hydrogen atom, or a mixture of said caffeoylquinic acids.

5 Claims, No Drawings

DEPIGMENTING COSMETIC AND/OR DERMATOLOGICAL COMPOSITION CONTAINING A DI- OR TRI-CAFFEOYLQUINIC ACID, OR A MIXTURE THEREOF

The present application concerns a depigmenting cosmetic or dermatological composition containing, as an active ingredient, at least one di- or tri-caffeoylquinic acid. The composition according to the invention is intended to whiten skin or to treat pigmentation spots.

It will be remembered that the skin pigmentation-formation mechanism, i.e., the melanin-formation mechanism, is especially complex and entails the following main steps, indicated schematically:

Tyrosine → Dopa → Dopaquinone → Dopachrome → Melanins.

tyrosinase being the basic enzyme involved in this series of reactions.

The substances most widely used at present as depigmenting agents are, most notably, hydroquinone and its derivatives, and especially its ethers, e.g., hydroquinone monomethyl ether.

While these compounds do posses a degree of efficacy, they do, unfortunately, produce side-effects, thereby making their use problematical, and indeed dangerous.

Thus, hydroquinone, whose use is moreover restricted to a concentration of 2%, is an especially irritating compound and cytotoxic for melanocytes, whose replacement, whether total or partial, has been considered by numerous authors.

The use of various other substances, in particular caffeic acid and/or its esters and amides, has, therefore, been suggested. These caffeic acid- or derivative-based compositions form the object of French Patent No. 86,13774 (2,653,336).

Natural substances, including arbutoside and methylarbutoside, have also been proposed. These compositions form the object of French Patent No. 85,04288 (2,577,805).

It is an established fact that a substance produces a depigmenting action if its acts directly on the vital processes of the epidermal melanocytes, where melanogenesis is normally carried out and/or if it interferes with one of the steps involved in melanin biosynthesis, either by inhibiting any of the enzymes involved or by inserting itself as structural analogue in the path of synthesis, which may thus become blocked, thereby producing the depigmenting effect.

The topical use of efficacious, non-harmful depigmenting substances is a goal particularly sought after in order to treat localized hyperpigmentation by melanocytic hyperactivity, such as idiopathic melasmas occurring during pregnancy (mask of pregnancy, or chloasma) or melasmas secondary to estro-progesterone contraception, localized hyperpigmentation caused by hyperactivity and benign melanocytic proliferation, such as age spots, called actinic lentigo, cases of accidental hyperpigmentation, such as photosensitization and cicatrization subsequent to lesions, as well as certain leukodermias, such as vitiligo in which, by virtue of the inability to repigment injured skin, the normal remaining skin areas are depigmented so as to give the entirety of the skin a homogeneous whitish tint.

After a great deal of work performed on various natural substances, it has been found that some caffeoyl quinic acids produced a depigmentation action which is particularly marked or appreciably greater than that of caffeic acid or its alkyl esters and than that of other conventionally-known depigmenting substances, such as hydroquinone.

These depigmenting properties have been brought to light using the in vitro test of inhibition of tyrosinase activity.

Thus, the present invention concerns a depigmenting cosmetic or dermatological composition containing, as an active ingredient, at least one di- or tri-caffeoylquinic acid corresponding to the general formula (I):

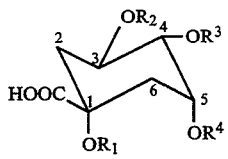

in which:

$R_1$, $R_2$, $R_3$, and $R_4$ represent a hydrogen atom or the caffeoyl radical, hereinafter termed CAF, corresponding to the formula:

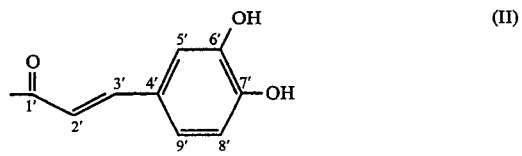

provided that at least two, and at most three, of the $R_1$, $R_2$, $R_3$, and $R_4$ radicals represent the CAF radical, but excluding $R_1$ and $R_4$ as both simultaneously representing the CAF radical and $R_2$ and $R_3$ as both simultaneously representing a hydrogen atom, or a mixture of said caffeoylquinic acids.

Among the compounds according to the invention and corresponding to formula (I), mention may be made of:

-4,5-di-caffeoylquinic acid
-3,5-di-caffeoylquinic acid
-1,3-di-caffeoylquinic acid
-3,4-di-caffeoylquinic acid
-3,4,5-tri-caffeoylquinic acid, and mixtures thereof.

Most of the compounds covered by the general formula (I) belonging to the compositions according to the invention have been described in the literature, in particular as constituents of Chrysothamnus Paniculatus, by Timmermann et al. in J.NAT.PROD., 83, Vol. 46(3), pp. 365–368.

The beneficial properties of some of these compounds have promoted their use in popular medicine (extracts from Argentine species of ASTERAGEAE; see ACTA FARM. BONAERENSA, 89, Vol. 8(1), pp. 3–9).

They have also been described as anti-allergy agents in Japanese Patent No. JP 88-218619, and as anti-influenza agents in Japanese Patent No. JP 85-243016, when they are obtained by methanol extraction from Helianthus Annus seeds.

The compositions according to the invention normally contain a concentration of active ingredient corresponding to formula (I) of between 0.01 and 15% by weight, and preferably between 0.1 and 8% by weight, of the total weight of the composition.

The compositions according to the invention may exist in various forms, in particular as aqueous or hydroalcoholic solutions, oil-in-water or water-in-oil emulsions, or as emulsified gels.

The compositions according to the invention preferably exist as a lotion, cream, milk, gel, mask, or as vesicular dispersions, in which the vesicles may be formed from ionic lipids (liposomes) and/or non-ionic lipids.

In the emulsions, the fatty phase may consist of a vegetable or animal oil, a mineral oil, or a synthetic oil.

The vegetable or animal oils, whether modified or not, include sweet almond oil, avocado oil, castor oil, olive oil, jojoba oil, perhydrosqualene, oil of Calophyllum, lanolin and its derivatives, sunflower oil, wheatgerm oil, sesame oil, peanut oil, grape seed oil, soybean oil, colza oil, safflower oil, coconut oil, corn oil, hazelnut oil, karite butter, Shorea robusta grease, palm oil, and apricot pit oil.

The mineral oils which may be mentioned include vaseline oil, and among the synthetic oils, ethyl and isopropyl palmitates, alkyl myristates, such as isopropyl, butyl, cetyl myristate, hexyl stearate, triglycerides of octanoic and decanoic acids (e.g., product sold under the tradename "Miglyol" ® by the Dynamit Nobel Company), cetyl ricinoleate, stearyl octanoate (purecellin oil), hydrogenated polyisobutene, and waxes such as ozokerite.

The fatty excipient may also contain certain compounds considered to be fatty products, i.e., long-chain alcohols, such as cetyl alcohol, stearyl alcohol, myristic alcohol, hydrostearyl alcohol, oleic alcohol, or isostearyl alcohol.

Silicone oils may be mentioned in the category of synthetic oils. Among these, preference is given to cyclopentadimethylsiloxane, in particular the product sold under the tradename "Volatil Silicon 71.58 ®" by Union Carbide, and to alkyldimethicone copolyol, especially the product sold under the tradename "Abil WE 09 ®" by the Goldschmidt Company.

The cosmetic or dermatological compositions according to the invention may well contain other wide-used ingredients, such as humectants, preservatives, coloring agents, perfumes, and penetrants, such as diethyelenglycol monoethylether.

These compositions are applied topically in quantities corresponding to the customary doses for the composition in question (i.e., gels, creams, lotions, etc.). For example, as regards creams, use is made of 0.5 to 3 mg, and, in particular 1 to 2 mg of cream per $cm^2$ of skin and per application, at a frequency of two applications per day.

PREPARATION OF THE COMPOUNDS ACCORDING TO THE INVENTION BY EXTRACTION FROM THE DRIED BARK OF SCAEVOLA KOENIGII, GOODENIACEAE, A MALAYAN PLANT 100 g of dried bark from Scaevola koenigii Goodeniaceae harvested in Malaya are treated using a fourfold methanol-extraction process (temperature 50°–60° C.). The methanol filtrates are brought together and evaporated to dryness. Starting with 100 g of dried bark, 18.5 g of an extract (i.e., a yield of 18.5%) are obtained and subjected to various treatments, as indicated below in Table I, in order to obtain a mixture of di- and tri-caffeoylquinic acids.

Caffeoylquinic acid derivatives, which produce an action on tyrosinase, are separated from the other compounds by adjusting the pH. Because of the existence of a carboxylic acid function in these compounds, their solubility in water or butanol depends on the pH of the medium. When the pH exceeds 7, the acid exists as a salt (RCOO) which dissolves in water. On the other hand, it is soluble in butanol when the pH is lower than 6. Consequently, it may be transferred from water to butanol by adjusting the pH of the medium.

TABLE 1

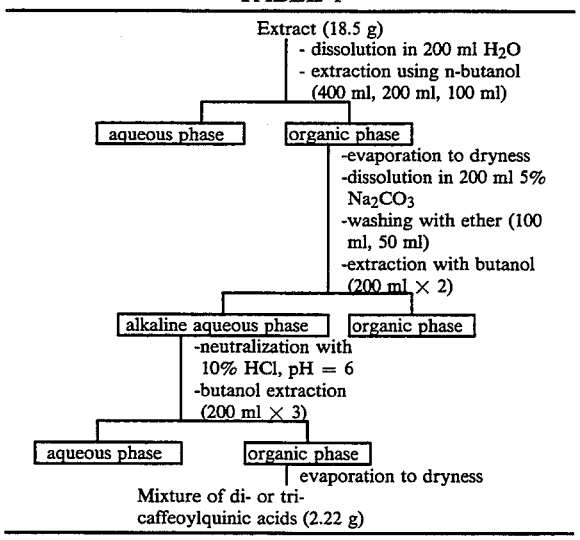

18.5 g of the raw extract are dissolved in 200 ml of water. Extraction using n-butanol is performed three times (400, 200, and 100 ml). The butanol phases brought together are evaporated to dryness and taken up in 200 ml of a 5% $Na_2CO_3$ solution. The alkaline phase is washed with ether (100, 50 ml), then extracted using two times 200 ml of butanol. The alkaline phase is then neutralized using 10% HCl until a pH of 6 is achieved, then extracted once again with butanol. The butanol phases brought together are evaporated to dryness. 2.22 g of a mixture of di- and tri-caffeoylquinic acids are obtained in yellow powder form.

Starting with this mixture, preparative HPLC is used to isolate different fractions whose compounds have been identified structurally by means of $^1$HRMN in deuterized methanol and mass spectrum.

The compounds thus isolated are basically those listed previously and are obtained in yields which vary as a function of structure.

The conditions for the preparative HPLC are as follows: Prep Pak -45×300 mm, delta Pak $C_{18}15$ μm. Flow Rate: 80 ml/min. Elution solvent A: 25% MeOH, 1% acetic acid. Elution solvent B: 40% MeOH, 1% acetic acid. Linear gradient from solvent A to solvent B during 30 minutes. Next, elution with 100% solvent B during 50 minutes.

In Vitro Analysis

The di- and tri-caffeoylquinic acids corresponding to general formula (I) have been studied comparatively with caffeic acid in equivalent molar quantities in the in vitro inhibition test of tyrosinase activity.

In this test, visible spectrometry at 475 mn is used to monitor the quantity of dopachrome formed during the chain of reactions by which tyrosine is transformed into melanins. These reactions are catalyzed in vitro using fungal tyrosinase in the presence of a reducing co-substrate (e.g., a small quantity of L-dopa) in order to initiate the hydroxylation reaction of L-tyrosine into L-dopa, which is then catalytically oxidized into dopaquinone, and then into dopachrome which is, an intermediate product, prior to the non-enzymatic oxidation reactions leading to melanin formation.

Accordingly, the concentration of dopachrome formed over time is measured in the presence and absence of the inhibitor.

The inhibition effect is expressed by the lowering of the maximum quantity of dopachrome formed (value of the optical density at 475 nm read on the flat part of the curve) in relation to the quantity obtained in the absence of the inhibitor.

For each compound, the content in micromoles per liter leading to 50% inhibition of the tyrosinase (IC 50) is measured.

EXPERIMENTAL METHODOLOGY

Reagents

A—Phosphate buffer 0.1M pH=6.5 (composition for 200 ml of buffer: 68.5 ml of $NaH_2PO_4$ 0.2M + 31.5 ml of $Na_2HPO_4$ 0.2M + 100 ml of water)

B—Mother solution of L-tyrosine at $2 \times 10^{-3}$M in A

C—Mother solution of L-dopa at $10^{-4}$M in A

D—Mother solution of fungal tyrosinase at 2,400 units/ml in A

E—Mother solution of the inhibitor at $10^{-2}$M in ethanol (solutions C and D must be prepared the same day).

Results reference trough:
3 ml of A test trough:
1.75 ml of A+1 ml of B
0.1 ml of C
0.1 ml of E homogenize and establish equilibrium at 25° C.
add 0.05 ml of D to the test trough
mix rapidly and observe the kinetics by measuring absorption at 475 nm as a function of time.

TABLE II

| Compounds | IC 50 |
| --- | --- |
| Caffeic acid (reference) | 530 |
| 4,5-di-caffeoylquinic acid | 45 |
| 3,5-di-caffeoylquinic acid | 52 |
| 1,3-di-caffeoylquinic acid | 47 |
| 3,4-di-caffeoylquinic acid | 85 |
| 3,4,5-tri-caffeoylquinic acid | 29 |

As can be seen, the di- and tri-caffeoylquinic acids belonging to the compositions according to the invention produce a melanogenesis-inhibiting activity that is clearly greater than that of caffeic acid.

Several examples of cosmetic/dermatological compositions according to the invention will now be given as non-limiting illustrations.

COSMETIC OR DERMATOLOGICAL COMPOSITIONS

Example 1: Lotion

| | |
| --- | --- |
| Alcohol | 50% |
| Polyoxyethyleneglycol (PEG 8) | 30% |
| Ethoxydiglycol | 5% |
| Glycerine | 5% |

| -continued | |
| --- | --- |
| Water | 2% |
| 1,3 di-caffeoylquinic acid | 8% |

Example 2: Water-in-Oil Emulsion

| | |
| --- | --- |
| Propyleneglycol | 10% |
| 3,4,5-tri-caffeoylquinic acid | 4% |
| Vaseline oil | 2% |
| Alkyldimethicone copolvol. sold under the tradename ABIL $WE^{09}$ ® by the Goldschmidt Company | 3% |
| Preservative | 0.2% |
| Perfume | 0.1% |
| Water qsp | 100% |

Example 3: Oil-in-Water Emulsion

| | |
| --- | --- |
| Propyleneglycol | 10% |
| 4,5-di-caffeoylquinic acid | 4% |
| Vaseline oil | 20.5% |
| Isostearate sorbitan | 5% |
| Stearyldimethylbenzylammonium hectorite, sold under the tradename Miglyol Gel ® by the Huls Company | 5% |
| Triglycerides of capric and caprylic acid | 1% |
| Preservative | 0.2% |
| Perfume | 0.1% |
| Water qsp | 100% |

Example 4: Preparation of Liposomes in Serum Formulation

In a round one-liter flask, the following products are weighed:

| | |
| --- | --- |
| Soy lecithin, sold under the tradename Lipoid S75 ® by the Lipoids Company | 3.0 g |
| 3,4-di-caffeoylquinic acid | 0.3 g | which are dissolved in 100 ml of a mixture of chloroform-methanol solvents in a ratio of 2/1.

The solvent is evaporated off using a rotary evaporator, and the last traces of solvent are removed by circulating using a vane pump for one hour. The combination of lipids obtained is placed in contact with 60 g of demineralized water containing 1 g of glycerine, and the mixture is homogenized at 40° C. by means of a Virtis homogenizer.

The formula is completed by adding the following products:

| | |
| --- | --- |
| Methyl parahydroxybenzoate | 0.2 g |
| Carboxyvinyl acid polymer sold under the tradename Carbopol 940 ® by the Goodrich Company | 0.1 g |
| Triethanolamine qs | pH = 6 |
| Water qsp | 100 g |

Thus, an opalescent fluid serum, but one which does not drain off, is obtained.

Example 5: Preparation of Non-Ionic Vesicles in a Cream Formulation

In a round 100 ml flask, the following products are weighed:

Non-ionic lipid substance having the following formula:

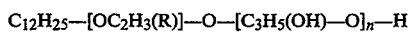

where $OC_2H_3(R)$ is formed by a mixture of the radicals:

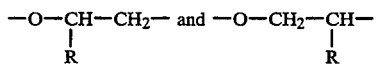

and $C_3H_5(OH)-O$ is formed by a mixture of the radicals:

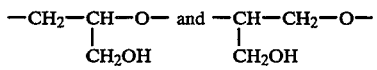

where n=6;

| | |
|---|---|
| and where R is a mixture of the radicals $C_{14}H_{29}$ and $C_{16}H_{33}$. | 0.9 g |
| Sodium acylglutamate HS21 ® (Sold by the Ajinmoto Company) | 0.1 g |
| 3,4,5-tri-caffeoylquinic acid | 0.1 g | which are dissolved in 30 ml of a mixture of chloroform-methanol solvents in a ratio of 2/1.

The solvent is evaporated using a rotary evaporator, and the last traces of solvent are removed by using a vane pump for one hour.

The combination of lipids obtained is placed in contact with 40 g of demineralized water containing 3 g of glycerine, and the mixture is homogenized at 40° C. using a Virtis homogenizer.

10 g of perhydrosqualene are then added, and the mixture is homogenized at ambient temperature using the Virtis homogenizer.

The formulation is completed by adding the following products:

| | |
|---|---|
| Methyl parahydroxybenzoate | 0.1 g |
| Carboxyvinyl polymer, sold under the tradename Carbopol 940 ® by the Goodrich Company | 0.4 g |
| Triethanolamine qs | pH = 6 |
| Water qsp | 100 g. |

A thick white cream is obtained.

What is claimed is:

1. Depigmenting cosmetic or dermatological composition, consisting essentially of in a suitable cosmetic or dermatological carrier from 0.001 to 15% by weight of at least one di- or tri-caffeoylquinic acid corresponding to the general formula (I):

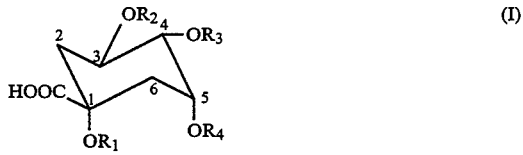

in which: $R_1$, $R_2$, $R_3$ and $R_4$ represent a hydrogen atom or the CAF radical corresponding to the formula:

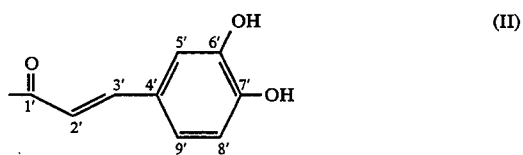

provided that at least two, and at most three, of the $R_1$, $R_2$, $R_3$ and $R_4$ radicals represent the CAF radical, with the proviso that:

(i) $R_1$ and $R_4$ do not represent CAF when $R_2$ and $R_3$ are hydrogen, (ii) $R_2$ and $R_4$ do not represent CAF when $R_1$ and $R_3$ are hydrogen, and (iii) $R_3$ and $R_4$ do not represent CAF when $R_1$ and $R_2$ are hydrogen; or a mixture of said caffeoylquinic acids.

2. The composition according to claim 1, wherein sad di- or tri-caffeoylquinic aid is selected from the group consisting of:
   -1,3-di-caffeoylquinic acid
   -3,4-di-caffeoylquinic acid
   -3,4,5-tri-caffeoylquinic acid, and mixtures thereof.

3. The composition according to claim 1, wherein said di- or tri-caffeoylquinic acid is present in a concentration of between 0.1 and 8% by weight the total weight of the composition.

4. The composition according to claim 1, wherein said composition is a lotion, cream, milk, gel, mask, or vesicular dispersions formed from ionic lipids and/or non-ionic lipids.

5. Composition according to claim 1, wherein said composition further contains in addition at least one cosmetic or dermatological ingredient selected from the group consisting of humectants, preservatives, coloring agents, perfumes, and penetrants.

* * * * *